July 14, 1942. R. L. BYRUM Plant Pat. 531
ROSE PLANT
Filed Jan. 16, 1942
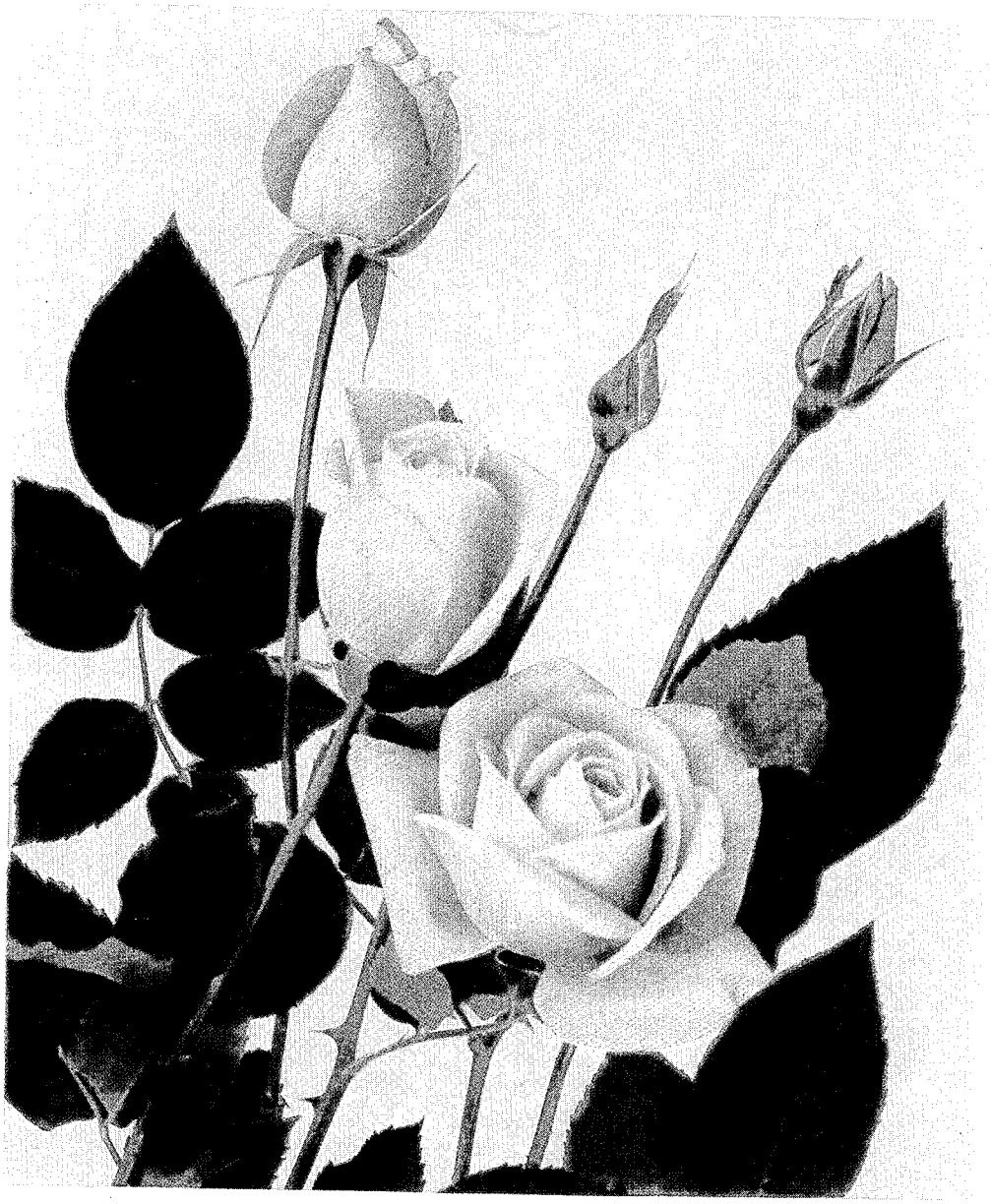
Inventor
Roy L. Byrum
By Robbins & Robb
Attorneys Patented July 14, 1942

UNITED STATES PATENT OFFICE

531

ROSE PLANT

Roy L. Byrum, Richmond, Ind., assignor to Joseph H. Hill Company, Richmond, Ind., a corporation of Indiana Application January 16, 1942, Serial No. 427,047

1 Claim. (Cl. 47—61)

The present invention relates to a new and distinct variety of rose plant, the result of a definite effort to produce a new rose which would combine in it the good qualities of its parents, and more particularly greater productivity than is characteristic of its pollen parent.

In carrying out my objective, I crossed the two known varieties "Chieftain" (Plant Patent No. 150) and "Sweet Adeline" (Plant Patent No. 6), and thereby obtained a new variety unlike any greenhouse forcing variety known to me. While this new rose retains the shape of bud of its seed parent, growth, and large size of its pollen parent, it differs materially from both in that it produces unusually large canes and foliage for a greenhouse forcing variety, and, moreover, the flowers show an unusual combination of color tones or shades as the blooms open. Color tones similar to those of "Sweet Adeline," influenced by the introduction of the "Chieftain" color, now comprise a combination unlike that of "Sweet Adeline."

The following is a detail description of this new rose, color terminology being in accord with Ridgway's Color Standard and ordinary dictionary meaning:

Type: Bush; greenhouse; seedling.
Class: Hybrid tea.
Parentage: Seedling.
*Seed Parent.*—"Chieftain."
*Pollen Parent.*—"Sweet Adeline."
Propagation: Holds its distinguishing characteristics through succeeding propagations by cuttings, grafting, and budding.

*Flower*

Locality where grown: Richmond, Indiana.
Flowers borne: Single to stem; in irregular cluster; on strong, long stems.
Quantity of bloom: Free in greenhouse.
Continuity: Continuous.
Fragrance: Slight; tea.
Bud:
*Peduncle.*—Long; heavy; erect; stiff; medium green; entirely smooth; numerous green prickles and thorns.
*Before calyx breaks.*—*Size*—large. *Form*—short; pointed; ovoid; with a conspicuous neck; with foliaceous appendages on the surface of the bud; with much-cut foliaceous parts extending beyond the tip of the bud equal to three-fourths or more of its length.
*As calyx breaks.*—Eugenia Red, Plate XIII, also showing some Acajou Red, Plate XIII.
*As first petal opens.*—*Size*—large. *Form*—long; ovoid. *Color,* outside: Base—Pale Lemon Yellow, Plate IV, changing to Rose Doree, Plate I, penciled with Acajou Red, Plate XIII. Inside: base—Lemon Chrome, Plate IV, changing to Rose Red, Plate XII, for balance of petal.
*Opening.*—Opens up well.
Bloom:
*Size, when fully open.*—Very large; five inches to six inches.
*Petalage.*—Very double; from fifty to fifty-five petals; arranged irregularly.
*Form.*—Very full; becoming, cupped; petals remaining at first cupped; becoming later, at maturity, loosely rolled outward.
Petals: Thick; leathery; inside, satiny; outside, shiny.
*Shape.*—Outside—obovate; scalloped with apex flat with one notch. Intermediate—obovate. Inside—lanceolate; scalloped irregular with one and two notches.

This description of a newly opened flower was made from a rose grown in a greenhouse in the month of October, 1941, at Richmond, Indiana:

*Color.*—Outside petal: outside surface—Rose Pink, Plate XII, slightly penciled with Deep Rose Pink, Plate XII; inside surface—Rose Color, Plate XII, penciled with Rose Red, Plate XII. Intermediate petal: outside surface—Rose Pink, Plate XII, very lightly penciled with Deep Rose Pink, Plate XII; inside surface—Rose Color, Plate XII, penciled with Rose Red, Plate XII. Inner petal: outside surface—Deep Rose Pink, Plate XII, blotched and striped with Pale Lemon Yellow, Plate IV; inside surface—Deep Rose Pink, Plate XII, overlaid with Rose Color, Plate XII.

This description was made from a rose that was open for three days in a greenhouse in the month of October, 1941, at Richmond, Indiana:

*Color.*—Outside petal: outside surface—Rose Pink, Plate XII, with heavy penciled streaks of Deep Rose Pink, Plate XII; inside surface—Deep Rose Pink, Plate XII, penciled and washed with Rose Red, Plate XII. Inside petal: outside surface—Rose Pink, Plate XII, washed and penciled with Deep Rose Pink, Plate XII; inside surface—Deep Rose Pink, Plate XII, penciled with Rose Color, Plate XII.
*General color effect.*—Newly opened flower—Rose Color, Plate XII. Three days open—Deep Rose Pink, Plate XII.

*Behavior.*—Persist.

*Flower longevity.*—Cut roses grown in greenhouse kept at living room temperatures five to six days in October.

*Reproductive organs*

Stamens: Many; arranged regularly about pistils, mixed with petaloids.

Filaments: Medium length; yellow reddish; most with anthers.

Anthers: Large; yellow; open at once.

Pollen: Abundant; gold.

Pistils: Medium number.

Styles: Uneven; medium length; thin; bunched.

Stigma: White.

Ovaries: Some protruding from calyx.

Hips: None as yet formed.

Sepals: Permanent; moderately long; spear-shaped; curled.

*Color.*—Inside—Pois Green, Plate XLI. Outside—Dark Dull Yellow Green, Plate XXXII.

Seeds: None as yet formed.

*Plant*

Foliage:

*Leaves.*—Compound of five leaflets; very abundant; very large; very heavy; leathery; wrinkled.

*Leaflets.*—Ovoid with apex acute; base obtuse; margin simply serrate.

*Color.*—*Mature*—upper surface—very Dark Green. Darker than Dark Dull Yellow Green, Plate XXXII. Under surface—very Light Green—Deep Dull Yellow Green, Plate XXXII. *Young*—upper surface—Green Bronze. Under surface—Light Green Bronze.

*Rachis.*—Heavy; upper side, grooved, hairy; under side, smooth, thorny.

*Stipules.*—Long; narrow; with medium long points turning out at an angle of less than 45°.

*Disease.*—Resistant to mildew and blackspot.

Growth:

*Habit.*—Bush; upright; much branched.

*Growth.*—Free; vigorous.

*Canes.*—Heavy.

*Main Stems.*—Dull Green Bronze and Rust. *Thorns*—several; medium length; hooked downward; with short, narrow base. *Prickles*—none. *Hairs*—none.

*Branches.*—Bright Green. *Thorns*—several; long; hooked downward; with long, narrow base. *Prickles*—none. *Hairs*—none.

*New shoots.*—Bronze Red. *Thorns*—several; straight; some hooked downward; with long, narrow base. *Prickles*—many; green. *Hairs*—many; green.

I claim:

A new and distinct variety of rose plant, characterized as to novelty by its distinctiveness as a greenhouse forcing variety, great productivity, unusually large canes and foliage, and novel color combination of its blooms, substantially as shown and described.

ROY L. BYRUM.